(12) United States Patent
Rogelj et al.

(10) Patent No.: US 6,498,189 B1
(45) Date of Patent: Dec. 24, 2002

(54) METHOD FOR INDUCTION OF L-SELECTIN SHEDDING

(75) Inventors: Snezna Rogelj, Socorro, NM (US); Teresa A. Bennett, Albuquerque, NM (US); Larry A. Sklar, Albuquerque, NM (US)

(73) Assignee: University of New Mexico, Albuquerque, NM (US)

( * ) Notice: Subject to any disclaimer, the term of this patent is extended or adjusted under 35 U.S.C. 154(b) by 0 days.

(21) Appl. No.: 09/442,940

(22) Filed: Nov. 18, 1999

Related U.S. Application Data

(63) Continuation-in-part of application No. 09/424,181, filed on Nov. 10, 1999.
(51) Int. Cl.$^7$ ............................................. A61K 31/285
(52) U.S. Cl. ...................................................... 514/504
(58) Field of Search ................................. 514/184, 504

(56) References Cited

U.S. PATENT DOCUMENTS 5,532,154 A    7/1996  Brown

FOREIGN PATENT DOCUMENTS

WO          98/51297    * 11/1998    ................. 514/504

OTHER PUBLICATIONS

Roussin European J. of Pharmacology 322 (1997) 91–6.*
Kalef, E. et al., Arsenical–Based Affinity Chromatography of Vicinal Dithiol–Containing Proteins: Purification of L1210 Leukemia Cytoplasmic Proteins and the Recombinant Rat c–erb A betal T3 Receptor, Analytical Biochemistry 1993, vol. 212, pp. 325–334.

Kahn et al., "Calmodulin Regulates L–Selectin Adhesion Molecule Expression and Function through a Protease–Dependent Mechanism," Cell, vol. 92, 809–818, Mar. 20, 1998.

Strausbaugh et al., "Painful stimulation suppresses joint inflammation by inducing shedding of L–selectin from neutrophils," Nature Medicine, vol. 5, No. 9, Sep. 1999.

* cited by examiner

Primary Examiner—Robert Gerstl
(74) Attorney, Agent, or Firm—Jagtiani + Guttag

(57) ABSTRACT

The invention provides anti-thiol reagents which inhibit enzyme activity of cell-associated protein disulfide isomerase (PDI) by oxidizing or blocking PDI active site vicinal thiol groups which normally participate in disulfide bond rearrangement of PDI substrates. Inhibition of this PDI function is particularly useful in blocking PDI-mediated entry of HIV or other virions into a host cell, as well as inhibiting lymphocyte traffic through the lymph nodes. The invention further provides an assay for the identification of such PDI inhibitors based on the discovery that inhibitors of the invention also induce shedding of the leucocyte L-selectin adhesion molecule. The invention additionally provides for suppression of inflammation and of lymph node entry by calmodulin antagonists that, like PDI inhibition, cause leukocyte L-selectin shedding.

6 Claims, 6 Drawing Sheets

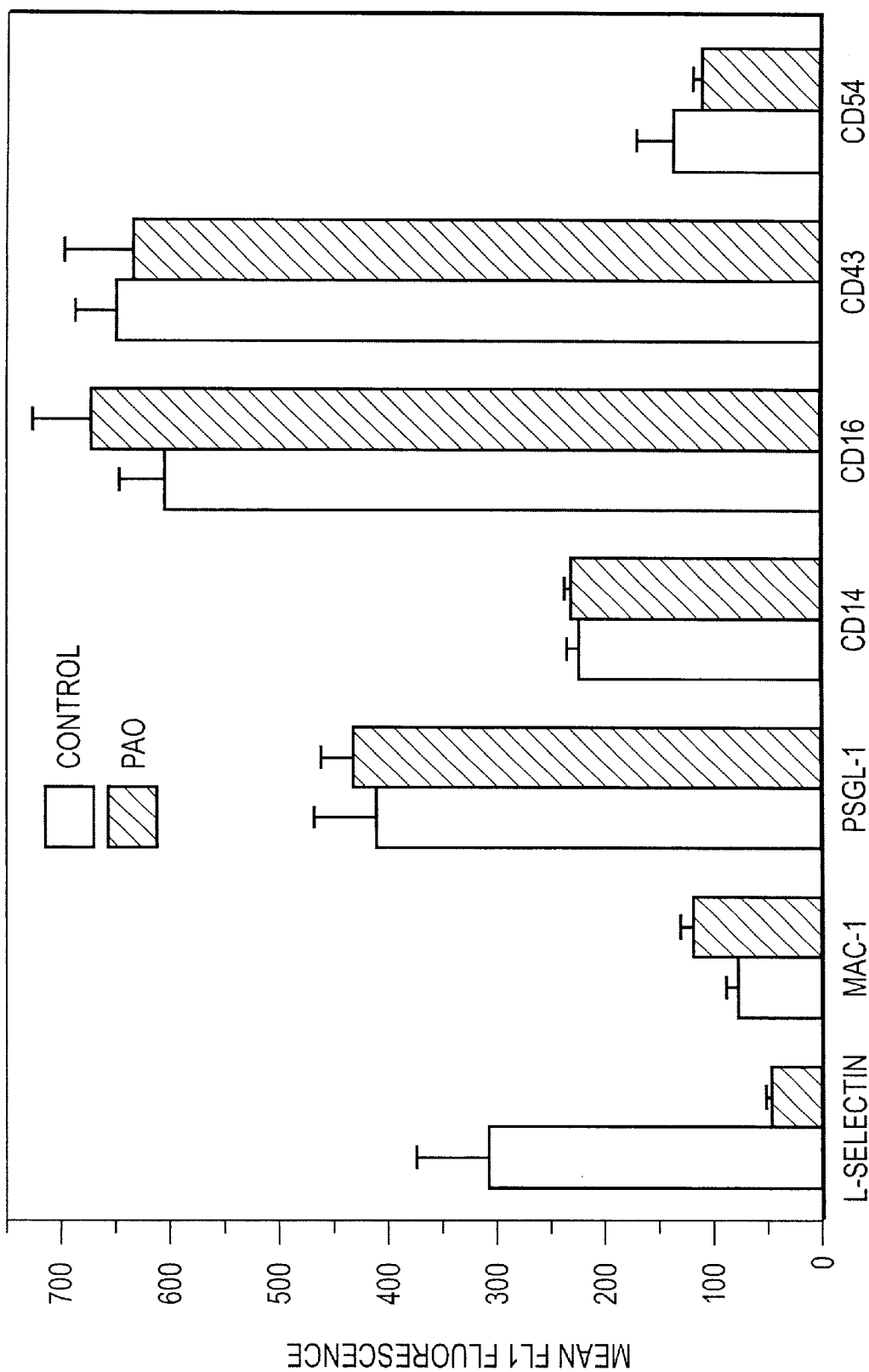

METHOD FOR INDUCTION OF L-SELECTIN SHEDDING

CROSS-REFERENCE TO RELATED APPLICATIONS

The present application is a continuation-in-part of a U.S. patent application Ser. No. 09/424,181 entitled "Inhibition of Cell Surface Protein Disulfide Isomerase" to Rogelj et al. filed Nov. 10, 1999, the entire contents and disclosure of which is hereby incorporated by reference.

BACKGROUND OF THE INVENTION

The invention relates to anti-thiol reagents which inhibit enzyme activity of cell-associated protein disulfide isomerase (PDI) by oxidizing or blocking PDI active site vicinal thiol groups which normally participate in disulfide bond rearrangement of PDI substrates. Inhibition of this PDI function is particularly useful in blocking PDI-mediated entry of HIV or other virions into a host cell.

The present invention also relates to anti-inflammatory agents.

The invention further relates to an assay for the identification of such PDI inhibitors based on the discovery that inhibitors of the invention also induce shedding of the leukocyte L-selectin adhesion molecule.

The invention further relates to the use of calmodulin antagonist reagents to induce L-selectin shedding.

1. Field of Art

PDI (protein disulfide isomerase) is a constitutive intracellular protein that is also found to be expressed on the surface of many mammalian cell types, including immune system cells, hepatocytes, and platelets. Like other members of the thyredoxin superfamily of proteins, PDI is a multi-functional redox-sensitive protein that catalyzes oxidation-reduction reactions via a vicinal dithiol-dependent disulfide-sulfhydryl interchange between its internal vicinal dithiol (Cys-Gly-His-Cys) active sites and the disulfide bonds of its substrates to promote their reconfiguration. PDI recognizes the side chains of cysteine residues in its substrates, and it is its two vicinal dithiol groups, two on each of two identical PDI subunits, that are critical for its enzymatic isomerase function, in particular its broad specificity for correcting the configuration of a large spectrum of proteins as needed. For example, PDI is present in the endoplasmic reticulum of most cells, where it is believed to mediate co- and post-translational modifications of nascent proteins with incorrect sulfide bonds; it is also present in certain protein complexes such as triglyceride transfer protein complex (MTP) wherein it maintains the complex in a catalytically-active state and inhibits complex aggregation. Membrane PDI catalyzes the cleavage of disulfide bonds during the earliest stages of endocytosis, and activates diphtheria toxin by catalyzing cleavage of this disulfide-linked dimer. PDI also catalyzes the isomerization of thrombospondin (TSP) disulfide bonds, thereby profoundly modulating TSP-ligand binding activity. Both TSP and PDI are released by activated platelets; PDI is also released by degranulated neutrophils (*J Cell Physiol.* 144: 280, 1990).

Other known PDI functions include the recognized ability of PDI to modulate certain adhesive interactions. While PDI isomerase activity affects, for example, the adhesive properties of TSP, PDI is additionally a "chaperone" for some proteins by means independent of its catalytic activity. One of these chaperone functions has been attributed to PDI binding in a complex formation with proteins which have a tendency to aggregate in the denatured state. Association with PDI prevents this aggregation by promoting appropriate folding of the associated protein. PDI in MTP complexes inhibits MTP aggregation, and a PDI homolog (cognin) plays a role in the adhesion-dependent aggregation of retinal cells.

2. Discussion of Related Art

Of particular relevance to the present invention is the involvement of PDI in the shedding of the human thyrotropin (TSH) receptor ectodomain (*Biochem,* 35:14800, 1996). In a two-step process, a matrix metalloproteinase first cleaves the receptor into two subunits (an α-extracellular subunit and a β-transmembrane subunit) linked by a disulfide bridge. The α-extracellular subunit is then shed from the cell membrane as a result of PDI-mediated reduction of the disulfide bridge(s) connecting it to the β-transmembrane subunit. However, in contrast to the PDI-mediated L-selectin shedding mechanism according to the present invention, the TSH shedding mechanism requires PDI isomerase activity, and inhibition of PDI activity with known PDI inhibitors such as DTNB (5,5'-dithiobis(2-nitrobenzoic acid), bacitracin, or anti-PDI antibodies to prevent the shedding (release) of the TSH α-subunit.

Also of relevance is the known ability of PDI to mediate transmembrane carriage of proteins and virions into cells by rearrangement of their disulfide bonds. For example, the attachment of HIV to its host cell surface receptor CD4 via the viral glycoprotein gp 120 triggers a conformational change in gp 120/gp 41 resulting from a rearrangement of its critical disulfide bonds as catalyzed by PDI. Known PDI inhibitors (e.g., bacitracin, anti-PDI antibodies) block HIV entry into the cell cytoplasm to some extent, but they are very weak inhibitors of PDI isomerase activity in this clinical application (*PNAS USA* 91: 4559, 1994). The use of another known PDI inhibitor, DTNB (supra) to inhibit viral penetration into cells has been described (U.S. Pat. No. 5,532,154 to Brown); however, the recited activity of this compound in preventing HIV entry into cells is attributed by the patentee to inactivation of "virus-derived thiol reductase/protein disulfide isomerase", presumably encoded by and present on the virus itself.

The interaction of arsine oxide with certain proteins having active vicinal dithiol sites which undergo catalytic conversion to disulfides to form stable dithioarsenic derivatives is described in *Anal. BioChem* 212: 325–334 (1993). This reactivity was used by the authors to separate dithiols from monothiols and also from dithiol-containing proteins with low-affinity for arsine oxide.

SUMMARY OF THE PRESENT INVENTION

In a first aspect, the present invention provides a compound having the formula:

$$\underset{NR_3R_4R_5}{\overset{AsR_1R_2}{C_6H_4}}$$

wherein each of $R_1$ and $R_2$ is thioalkyl sulfonate, thioalkyl amine, alkyl sulfonate or $R_1$ and $R_2$ together are the same alkyl sulfonate; and each of $R_3$, $R_4$ and $R_5$ is nothing, H, alkyl, alkyl sulfonate, or aromatic sulfonate.

In a second aspect, the present invention provides a compound having the formula:

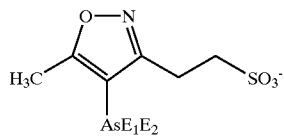

wherein each of $E_1$ and $E_2$, is thioalkyl sulfonate, thioalkyl amine, alkyl sulfonate or $E_1$ and $E_2$ together are the same alkyl sulfonate.

In a third aspect, the present invention provides a method for treating an inflammatory disease comprising: administering an anti-inflammatory agent to an individual in an amount sufficient to reduce an inflammation in the individual, wherein the anti-inflammatory agent comprises at least one PDI inhibitor.

In a fourth aspect, the present invention provides a method for treating an inflammatory disease comprising: administering an anti-inflammatory agent to an individual in an amount sufficient to reduce an inflammation in the individual, wherein the anti-inflammatory agent comprises at least one calmodulin antagonist.

DETAILED DESCRIPTION OF THE PREFERRED EMBODIMENTS

Definitions

Figure 1:
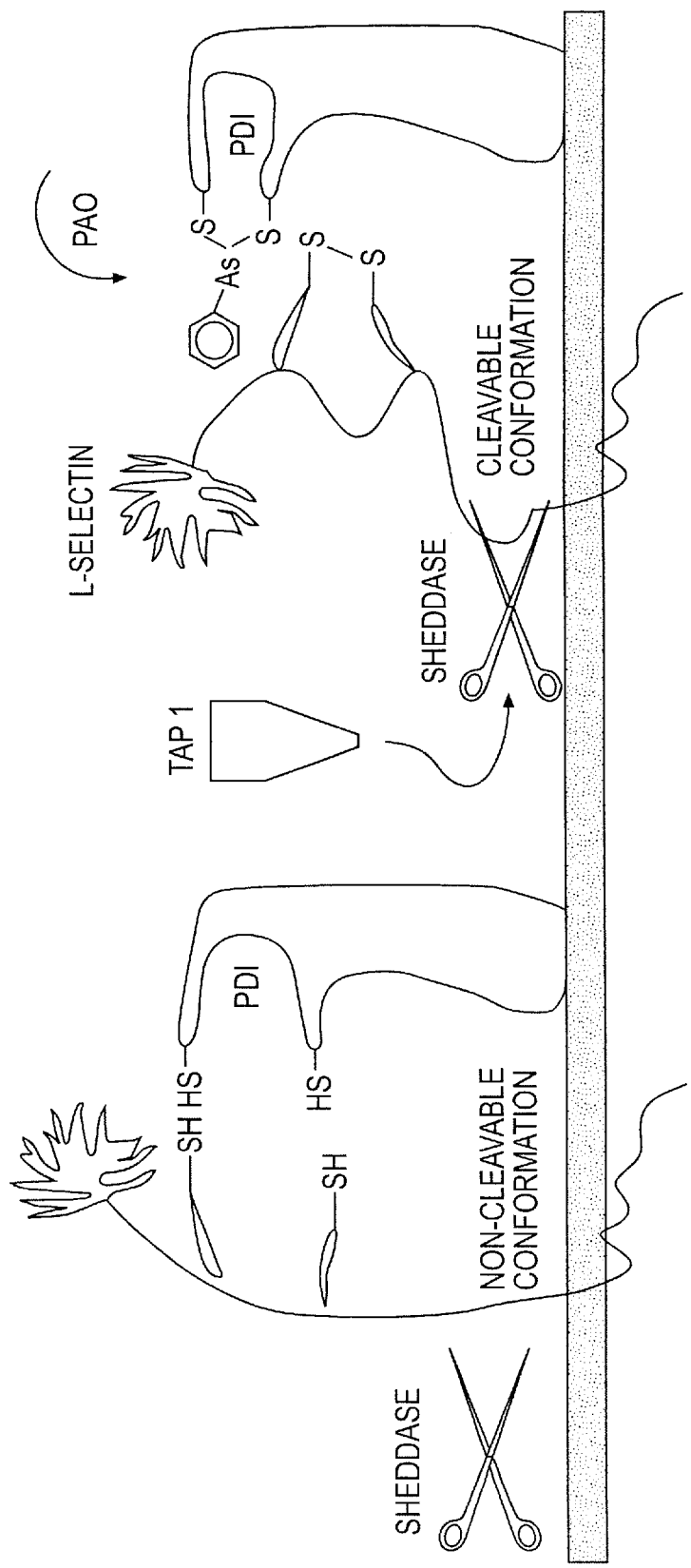
FIG. 1. Regulation of L-selectin shedding. Reduced cell surface PDI constitutively maintains L-selectin in the reduced, non-cleavable conformation. Chemical blockade or direct oxidation of the PDI vicinal dithiol active sites leads to a formation of a critical disulfide bridge within L-selectin molecule. The resulting conformation of L-selectin permits cleavage by the sheddase. In the presence of TAPI, L-selectin shedding is blocked.

For the purposes of the present invention, the term "compound" refers to both neutral compounds and charged ions, unless specified otherwise.

For the purposes of the present invention, the term "phenylarsine oxide derivative" includes any compound described below that is derived from phenylarsine oxide, including compounds having the formulas: A, B, C, D, E, A', B', C', D', E', etc.

For the purposes of the present invention, the term "PDI inhibitor" refers to an anti-thiol reagent which inhibits enzyme activity of cell-associated protein disulfide isomerase (PDI) by oxidizing or blocking PDI active site vicinal thiol groups which normally participate in disulfide bond rearrangement of PDI substrates. Many examples of PDI inhibitors, such as phenylarsine oxide (PAO) and phenylarsine oxide derivatives, suitable for use in the method of the present invention are described below For the purposes of present invention, term "calmodulin antagonist" refers to any compound that interferes with calmodulin binding to any calmodulin receptor. These include phenothiazine derivatives such as trifluoperazine and chlorpromazine as well as bis-chlorophenylethanes such as DDT, methoxychlor and dicofol, and gossypol and its derivatives, etc.

For the purposes of the present invention the term "individual" refers to either an individual person or animal who is treated according to a method of the present invention.

For the purposes of the present invention, the term "inflammatory disease" includes all diseases causing an inflammation, including: septic/toxic shock, acute respiratory distress syndrome (ARDS), asthma, dermatitis (contact hypersensitivity), peritoneal inflammation, delayed-type hypersensitivity reactions, reperfusion injury, burn injury, transplant rejection, chronic inflammatory disease, hemorragic-traumatic shock, metastases, etc.

For the purposes of the present invention, the term "$C_{1-8}$ alkyl" refers to a straight or branched chain alkyl moiety having one to eight carbon atoms including for example, methyl, ethyl, propyl, isopropyl, butyl, sec-butyl, isobutyl, pentyl, dimethyl-propyl, hexyl, and octyl, and cognate terms (such as "$C_{1-8}$ alkoxy") are to be construed accordingly. Similarly, terms such as "$C_1$ alkyl", "$C_3$ alkyl", "$C_4$ alkyl", "$C_6$ alkyl" refer to a straight or branched chain alkyl moieties having 1, 3, 4 and 6 carbon atoms, respectively.

For the purposes of the present invention, the term "amine" refers to either a neutral amine radical or a positive amine radical ion, unless specified otherwise.

Formula A below includes an amine group that is a neutral amine radical. Formula D below includes an amine group that is a positive amine radical ion.

For the purposes of the present invention, the term "thioalkyl sulfonate" refers to a radical joined to As or N by a sulfur atom and including an alkyl group and a sulfonate group. An example of a thioalkyl sulfonate group in which both bonds of As are attached to the same thioalkyl sulfonate group is Formula F below.

For the purposes of the present invention, the term "thioalkyl amine" refers to a radical joined to As by a sulfur atom and including an alkyl and an amine group. An example of a thioalkyl amine group is either of the two radical groups joined to As in Formula G below.

For the purposes of the present invention, the term "alkyl sulfonate" group refers to a radical joined to As or N by a carbon atom and including an alkyl group and a sulfonate group. An example of an alkyl sulfonate group is the alkyl sulfonate group joined to As in Formula H below.

For the purposes of the present invention, the term "aromatic sulfonate" refers to a radical joined to N that includes an aromatic group and a sulfonate group. The aromatic group may be attached directly to N or may be attached to N through a $C_{1-8}$ alkyl group.

Description

L-selectin (CD62L) is a leukocyte cell surface adhesion molecule. It is critically involved in the recruitment of leukocytes to sites of inflammation and the homing of lymphocytes into lymph nodes. To access these target sites, leukocytes must first adhere to the vascular endothelium; and it is this adhesive process which is in part mediated by L-selectin. This adhesion is prevented when L-selectin is blocked or removed (shed) from the cell surface. Potent control of the inflammatory response and of the lymphocyte recirculation through the peripheral lymphoid tissues is achieved by removing L-selectin from leukocyte surface.

Leukocytes naturally release (shed) L-selectin under certain activating circumstances. This shedding is an important mechanism for regulating leukocyte adhesive, and thus inflammatory and lymph-node-homing, capacity. Two (potentially overlapping) biochemical pathways regulate L-selectin shedding: 1. A cell surface pathway. This pathway involves inactivation of protein disulfide isomerase (PDI or a closely related protein) with reagents that include dithiol-reactive compounds. These reagents, acting from the OUTSIDE of the cell, initiate a series of reactions that lead to the release of L-selectin from leukocyte cell surface; and 2. an intracellular pathway. This pathway involves inactivation of an intracellular protein calmodulin. Calmodulin antagonists, acting from INSIDE of the cell, initiate a series of reactions that lead to the release of L-selectin from leukocyte cell surface.

Activation of either or both of these pathways will lead to L-selectin shedding from leukocytes and prove to be anti-inflammatory.

In one preferred embodiment invention provides cell-surface protein disulfide isomerase (csPDI) inhibitors which block PDI-mediated disulfide rearrangement in PDI substrates. In particular, the invention provides (di)thiol-reactive reagents which react with active site vicinal dithiols of csPDI to inhibit the substrate disulfide bond rearrangement prerequisite for entry of the substrate into the cell.

The invention further provides calmodulin antagonists as inducers of L-selectin shedding. Calmodulin is a ubiquitous calcium binding protein that is found associated with L-selectin inside the cell. When calmodulin is prevented from binding L-selectin, L-selectin gets released from the cell surface. This has been shown independently by Julius Khan et al.(Kahn J. Walcheck B. Migaki G I. Jutila M A. Kishimoto T K. Calmodulin regulates L-selectin adhesion molecule expression and function through a protease-dependent mechanism. Cell. 92(6):809–18, Mar. 20, 1998) and by the present inventors (not published). A variety of calmodulin antagonists, included in Table 1 below, effectively promote L-selectin shedding from leukocytes.

There exists a broad spectrum of calmodulin antagonists, reviewed in Molecular Genetics & Metabolism. 64(3):161–8 (1998 July). The specificity and toxicity is particular for each of these calmodulin antagonists. Some effective and currently used pharmaceuticals have, subsequent to their medicinal implementation, been found to act as calmodulin antagonists (Chlorpromazine, an anti-psychotic tranquilizer and related phenothiazine drugs). Surprisingly, some potent pesticides (e.g. DDT) also display calmodulin antagonism.

The invention is in part predicated on the discovery that inhibitors according to the invention also promote shedding of the leucocyte adhesion molecule L-selectin, and screening protocols for identification of inhibitors within the scope of the invention based on this phenomenon are accordingly further provided.

The inhibitors of the invention are particularly useful for denying viruses requiring disulfide bond rearrangement for transmembrane passage to access host cell DNA for replication. The invention accordingly provides methods for inhibiting replication of such viruses, notably gag retroviruses including HIV virotypes, by disrupting their PDI-mediated cell entry mechanisms.

The invention additionally provides a two-pronged approach for prevention and treatment of PDI-mediated viral infection based on the observed contemporaneous inducement of L-selectin shedding and the inhibition of viral cell entry by the inhibitors of the invention.

Furthermore, induction of L-selectin shedding, promoted by either pathway (PDI inhibitors or by calmodulin antagonists) prevents lymphocyte homing that is pathogenic in the HIV disease. Similarly, induction of L-selectin shedding by either pathway provides for a potent anti-inflammatory treatment.

Pharmaceutical compositions containing the inhibitors of the invention and methods for treating or preventing viral infection in humans or other mammals, including periodic elevations of HIV or other viremia, are also provided. Combinations of these compositions and methods with other viral therapies are useful.

According to the invention, cell-surface PDI (csPDI) isomerase activity is effectively inhibited by thiol blocking agents (inhibitors) which covalently or non-covalently cross-link two or more free vicinal sulfhydryl groups of one or more PDI active site peptide sequences to form complexes stable in the cell environment. The —SH groups of the cysteine residues in the sequence Cys-Gly-His-Cys are exemplary. The inhibitors are preferably highly selective for PDI vicinal sulfhydryls and have sufficient affinity for these groups to compete successfully with the ligand to be denied access to these sites and prevent PDI-mediated isomerization of its disulfide bonds and its consequent reconfiguration for undesired biological activity. The sequence of PDI is known (*Nature* 317:6034; 267, 1985). Herein, "csPDI" and "PDI" are used interchangeably unless otherwise noted.

Inhibitors according to the invention are useful for inhibiting thiol-mediated csPDI isomerase activity with proper selection of inhibitors, and possibly one or more non-isomerase activities, such as the afore-mentioned "chaperone" activity. This includes both presently-known PDI isomerase and other activities and other cell-associated PDI activities yet to be discovered.

In one embodiment, the PDI inhibitors of the invention inhibit virion cell entry mediated by csPDI expressed on the plasma membrane of potential host cells, particularly gag retroviruses such as HIV virotypes. As described in further detail below, PDI inhibitors useful for this application can be directly identified by appropriate NIH protocols such as those described for HIV infra. Alternately, according to the invention, potentially useful PDI inhibitors are identified by screening for their ability to induce L-selectin shedding. The ability of the L-selectin shedding assay of the invention (Examples) to identify inhibitors of thiol-mediated csPDI activity is demonstrated in detail infra. This assay is based on the observation that a blockade of leucocyte csPDI oxido-reductive function induces a release of L-selectin, a cell surface adhesion molecule, and that the rate of L-selectin release is a direct reflection of the efficacy of the csPDI inhibitor. Therefore, measuring the amount of L-selectin released from leucocytes within a certain time period provides information regarding the potency of the putative csPDI inhibitor.

A detailed description of L-selectin shedding phenomena is given in *J Immun.* 156:3093–3097, 1996, the entire contents and disclosure of which is hereby incorporated by reference. Briefly, the L-selectin adhesion molecule mediates leucocyte recruitment to inflammatory sites and lymphocyte trafficking through the peripheral lymph nodes. In response to leucocyte activation, L-selectin is proteolytically released (shed) from the cell surface, disabling leucocytes from the subsequent L-selectin-dependent interactions. L-selectin shedding is sensitive to sulfhydryl chemistry and PDI (or a closely related protein) regulates the susceptibility of leucocyte L-selectin to shedding promoted by (di)thiol oxidizing or blocking reagents according to the invention. In contrast to known prior art shedding mechanisms such as those for TSH (supra), csPDI constitutively acts on L-selectin to maintain its disulfide bonds in a reduced, non-cleavable state; blockade of PDI permits reversion of these bonds to the oxidized, cleavable conformation for shedding. Thus, shedding is promoted by the instant inhibitors in direct relationship to the effect of the inhibitors on blocking csPDI function (FIG. 1). Since L-selectin is also present on lymphocytes and mediates their entry into peripheral lymph nodes, L-selectin shedding according to the invention also inhibits the movement of virally-infected lymphocytes into these nodes, preventing the establishment of viral reservoirs responsible for spreading the infection to uninfected lymphocytes. In chronically infected individuals, the inhibition of nascent, uninfected lymphocyte trafficking through the lymph node viral reservoirs would further prevent the exposure of these cells to the virus, and therefore the internal spread of HIV. Finally, by inducing the shedding of lymphocyte L-selectin, these reagents would ameliorate the lymphoadenopathy thought to be due to an increase in L-selectin expression, and therefore homing to the lymph nodes, by the abortively HIV-infected lymphocytes.

PAO (phenylarsine oxide), a trivalent arsenical inhibitor of the invention interacts with PDI vicinal dithiols and is most potent in inducing rapid shedding of L-selectin from isolated neutrophils, eosinophils, and lymphocytes, as well as from neutrophils in whole blood. PAO does not cause cell activation, nor does it interfere with integrin function or alter the expression of several other cell surface molecules at the lower concentrations that effectively induce L-selectin shedding. Further, PAO is not required to enter the cell to induce L-selectin shedding. TAPI, which has previously been shown to inhibit activation-dependent L-selectin shedding, is also capable of inhibiting PAO-induced L-selectin shedding. The Snezna L-Selectin Assay of the invention has been validated with human leucocytes but is anticipated to work as well with leucocytes of other species. In all cases, species-specific anti-L-selectin antibodies should be used for labeling. Although the assay can be carried out with either neutrophils or with lymphocytes, neutrophils appear to provide a faster and a more sensitive L-selectin shedding response. PDI inhibitors identified by this protocol are useful in the inhibition of PDI according to the present invention.

Inhibitors of the invention comprise agents which form stable complexes or derivatives by covalent or non-covalent binding with one or more active thiol groups of PDI to inhibit catalytic rearrangement of substrate disulfide groups. Both monothiol inhibitors (which inactivate single thiol groups) and dithiol inhibitors (which cross-link two thiol groups) are useful, especially inhibitors specific to PDI vicinal sulfhydryl groups, and act by blocking or oxidizing the groups. Preferred inhibitors for in vivo use comprise membrane impermeable inhibitors [denoted herein with an asterisk (*)], as this avoids toxicity resulting from undesirable effects of cell-permeable inhibitors on intra-cellular processes. More preferred for in vivo uses are asterisked inhibitors efficacious in evaluation protocols at relatively low concentrations (i.e., concentrations with respect to each other).

Typically, dithiol inhibitors will have greater efficacy as inhibitors, as they have been found to have greater potency at lower concentrations. This is important, as many of the inhibitors are potentially toxic to cells at high concentrations, especially cell-permeable inhibitors. Vicinal dithiol-reactive inhibitors will have a preference for the vicinal (closely spaced) dithiol (two reduced cysteines) sites such as those found in the active sites of PDI. It is known that the dithiol-reactive reagents are much less likely to interact with monothiol sites. (Reactivity with monothiol sites should generally be avoided as it would lead to loss of specificity and an increase in cytotoxicity.) Dithiol reactivity thus enhances specificity and potency while minimizing cytotoxicity. Using dithiol reagents such as PAO derivatives offers an additional advantage: they can be selectively removed from a target protein such as PDI with DMP (British Anti-Lewisite, a clinically-known heavy metal antidote) or the related (membrane-impermeable) DMPS, once the desired effect has been achieved. Such a reversal can be carried out if PAO(*) toxicity becomes an issue and PAO(*) needs to be flushed-out from the patient.

Exemplary inhibitors useful in the practice of the invention are set forth in TABLE 1, below.

TABLE I

COMPOUNDS THAT INDUCE L-SELECTIN SHEDDING FROM NEUTROPHILS
100% LOSS from cell surface in 10 min at 37 deg. at the approximate concentration:
(membrane-impermeable inhibitors are marked with *)

| | | |
|---|---|---|
| Thiol Blocking and Oxidizing reagents | | |
| PAO | –1 uM- | vicinal dithiol specific |
| PAO-DNP | –1 uM- | DNP added far from AsO group |
| Aminophenylmercuric acetate | 10 uM- | monothiol reactives activates MMPs |
| Nitroblue tetrazolium | 100 uM- | superoxide scavenger and oxidant |
| Hydrogen peroxide | 150 uM- | oxidant, effect inhibitable by excess DMPS |

TABLE I-continued

COMPOUNDS THAT INDUCE L-SELECTIN SHEDDING FROM NEUTROPHILS
100% LOSS from cell surface in 10 min at 37 deg. at the approximate concentration:
(membrane-impermeable inhibitors are marked with *)

| Compound | Concentration | Description |
|---|---|---|
| Monobromobimane mBBr | 100 uM- | thiol blocker (fluorescent as bound) |
| Dibromobimane bBBr | 100 um- | dithiol reactive, spacing differs from PAO |
| *DIDS | 200 uM- | thiol and amino-group reactive |
| N-ethylmaleimide | 250 uM- | thiol blocker |
| *Quaternary bromobimane qBBr | 300 uM- | membrane-impermeable mBBr |
| Iodoacetate IA | 300 uM- | thiol blocker, also depletes energy |
| *Mersalyl acid | 500 uM- | thiol-reactive via-HgOH |
| Thimerosal | 500 um- | thiol blocker, used as preservative |
| *DTNB | 1 mM- | thiol-blocker |
| PMSF | 1 mM- | attacks and blocks-SH (and OH) groups |
| Diamide | 1 mM- | thiol oxidizer/crosslinker, ADA analog |
| Azodicarbonamide | 1 mM- | blocks HIV infectivity, flour additive |
| Iodoacetamide | 10 mM- | thiol reagent, low efficacy (vs. 1A) surprising |
| Iodosobenzoate | 1 mM- | A dithiol oxidizing reagent just like PAO, but with Iodine instead of arsenic, causes direct oxidation of dithiols |
| Dithiol Reactive Ions: | | |
| Arsenic (As203) | 50 uM | |
| Cadmium (CdCl2) | 1 mM | |
| Antimony (Sb203) | 50 uM | |
| Other Reagents and Conditions: | | |
| *Dehydroascorbate | 1 M- | specifically and only reduced by PDI or glutaredoxin, would lead to net oxidation of PDI |
| Chlorpromazine | 50 mM- | blocks HIV infectivity at this concentration |
| Methoxychlor | 50 uM- | a pesticide, a calmodulin antagonist |
| DDT | 50 uM- | a pesticide, a calmodulin antagonist |
| Disulfiram (Antabuse) | 50 uM- | drug that induces alcohol aversion |
| *Thioredoxin | 50 ug/ml- | reductant at cell surface, poor isomerase, has biphasic effect on shedding |
| *Protein Disulfide Isomerase | 20 ug/ml- | effective isomerase at cell surface |
| Somatostatin | 200 uM- | peptide PDI inhibitor |
| UV irradiation | 10 min- | produces ROS, effect TAPI inhibitable |

Other exemplary inhibitors useful in the practice of the invention are set forth below. These tested inhibitors include both the (di)thiol reactive and calmodulin antagonists listed in table Table 1. Additional known (di)thiol reactive disulfide reagents to have comparable PDI inhibitory activities include the following vicinal di-thiol reactive/blocking reagents: 2,2'-dithiobis(4-methylthiazole), 2,2'-dithiobis(5-nitropyridine), N,N'-dithiobisphtalamide, 2,2'-dithiobisanline, 2,2'-dithiodibenzoic acid, and 5,5'Dithiobis(1-phenyl-1H-tetrazole). The method of the present invention can also employ all of the disulfide reagents listed in International Patent Application WO 96/09406, the entire contents and disclosure of which is hereby incorporated by reference. These reagents, which are (di)thiolreactive and potent inhibitors of PDI and thus potent inducers of L-selectin shedding, include: tetramethylthiuram disulfide; tetraethylthiuram disulfide; tetraisopropylthiuram disulfide; tetrabutylthiuram disulfide; dicyclopentamethylenethiuram disulfide; isopropylxanthic disulfide; O,O-diethyl dithiobis-(thioformate); benzoyl disulfide; benzoylmethyl disulfide; formamidine disulfide-2HCl; 2-(diethylamine)ethyl disulfide; aldrithiol-2, aldrithiol-4; 2,2-dithiobis(pyridine N-oxide); 6,6-dithiodinisotinic acid; 4-methyl-2-quinoyl disulfide; 2-quinoyl disulfide; 2,2-dithiobis(benzothiazole); 2,2-dithiobis(4-tert-butyl-1-isopropyl)-imidazole; 4-(dimethylamino)phenyl disulfide; 2-acetamidophenyl disulfide; 2,3-dimethoxyphenyl disulfide; 4-acetamidophenyl disulfide; 2-(ethoxycarboxamide)phenyl disulfide; 3-nitrophenyl disulfide; 4-nitrophenyl disulfide; 2-aminophenyl disulfide; 2,2-dithiobis(benzonitrile); p-tolyl disulfoxide; 2,4,5-trichlorophenyl disulfide; 4-methylsulfonyl-2-nitrophenyl disulfide; 3,3-dithiodipropionic acid; N,N-diformyl-L-cystine; trans-1,2-dithiano-4,5-diol; 2-amino-4-chlorophenyl disulfide; 5,5-dithiobis(2-nitrobenzoic acid); 2,2-dithiobis(1-naphtylamine); 2,4-dinitorphenyl p-tolyl disulfide; 4-nitrophenyl p-tolyl disulfide; thiamine disulfide, 4-chloro-3-nitrophenyl disulfide.

As alluded to supra, the inhibitors of the invention are especially useful in vivo for blocking entry of virions into targeted host cells by blocking an essential PDI-mediated step of their transmembrane process. Since some of the inhibitors useful in this process, such as PAO, also induce L-selectin shedding from lymphocytes and thus inhibit lymphocyte entry into peripheral lymph nodes, the establishment of reservoirs of transfected lymphoctyes is concurrently inhibited. This is an important advantage when treating viral infections characterized by lymphocyte infection such as HIV, since HIV-infected cells can each produce billions of virions daily and it is the subsequent entry of these virions into uninfected cells which propagates the disease.

Most of the inhibitors identified by the inventors to date, including cadmium, and trivalent arsenical and antimonial compounds work by blocking the vicinal cysteines in PDI active sites; however, some inhibitors may work by blocking PDI activity by a mechanism that is different from the thiol-mediated blockade of the Cys-Gly-His-Cys active sites. The inhibitors are generally not cell-specific (unlike, for example, fMLP for which CHO and lymphocytes are receptor negative), and are selected as the application requires as described herein. Cell-membrane impermeable inhibitors are typically selected for applications requiring minimization of toxicity as are the dithiol and dithiol-specific inhibitors, as these tend to be efficacious at lower relative concentrations. Monothiol and/or cell-membrane permeable inhibitors are, however, useful in the practice of the invention and may prove equal or superior to dithiol inhibitors in applications where a slight increase in cell toxicity is not a critical factor.

Pharmaceutical compositions containing the inhibitors of the invention are useful as prophylactics for immediate treatment on exposure to HIV or other PDI-dependent viruses and for treating established viral infection, including periodic elevations of HIV or other viremia. Treatment according to the invention along with other therapies is contemplated.

Compositions for parenteral administration comprise aqueous solutions of the inhibitors of the invention in an amount sufficient to provide a blood concentration of about 1 $\mu$M or less in whole blood. More potent inhibitors are contemplated to be effective at concentrations of about 0.1 $\mu$M or less. Suitable concentrations are readily determined by combining an inhibitor with a blood sample and selecting a concentration that induces PDI shedding from leucocytes, usually within about 20 minutes to 2 hours. depending upon inhibitor concentration. For intravenous administration, compositions comprising inhibitor and (at least mostly) water as solvent in concentrations of about 35 mg/ml of solvent are generally effective.

For example, 1 uM PAO (i.e., about 0.17 mg PAO/liter of blood) blocks PDI in whole human blood to the extent that 50% L-selectin shedding from neutrophils is induced in about 20 min. 10 uM (i.e., about 1.7 mg PAO/liter of blood) should induce complete shedding within about 20 min. Thus, administering sufficient PAO to attain 10 uM concentration of PAO in blood should fully block leucocyte csPDI. Since only a fraction of total body weight is blood (assume 10 liters in a 50 kg human), then 17mg of PAO is required for this effect. This translates to 17 mg/50 kg or about 0.35 mg PAO/kg body weight. A 100 kg human thus would require about 35 mg of PAO to attain "instantaneous" 10 uM blood concentration. PAO at these low concentrations is soluble in most aqueous media (the initial high concentration stock in DMSO can be diluted into aqueous buffer for in vivo use).

A recommended procedure for in vivo administration of PAO comprises preparing an injectable (for example, i.v.) aqueous stock of PAO containing 35 mg PAO/ml PBS. Depending on the weight of the patient, an appropriate volume is injected (e.g., a 70 kg person would receive about 0.7 ml of the preparation). To avoid local toxicity, this stock preparation can be diluted further and proportionally larger volume injected slowly to attain the same blood concentrations in a comparable period of time.

Similar calculations are carried out for the various PAO* inhibitors, and based on the predetermined concentration required to induce full shedding of L-selectin in whole blood. For example, 10 uM PAO* is required to obtain about the same results as 1 uM PAO, in whole blood. The required concentrations for treatment are thus 10 times higher, i.e., 3.5 mg PAO*/kg body weight. The injectable stock preparation should then be made up as 350 mg PAO*/ml PBS; a 70 kg human would need 0.7 ml of this stock preparation. In practice, lower concentrations might suffice, as these are high-end estimates. Concentrations should be kept to a minimum sufficient for effectiveness to minimize toxicity.

Of great advantage is that the inhibitors are readily soluble in aqueous media at the concentrations needed for effective administration for inhibiting PDI isomerase activity and/or virion entry into cells. Compositions can also be administered orally; oral compositions comprising excipient (s) and inhibitor in amounts which provide blood concentrations as described above are useful in the practice of the invention.

In addition to being able to treat viral infections, and in particular, HIV infections, phenylarsine oxide and the phenylarsine oxide derivatives of the present invention, such as compounds A, B, C, D, E, A', B', C', D', and E' described below, are useful as anti-inflammatory agents. Removal of L-selectin from the cell surface with phenylarsine oxide or the phenylarsine oxide derivatives of the present invention can have a profound beneficial impact in preventing many L-selectin dependent diseases such as inflammatory diseases, allergic diseases, graft rejection, metastases of lymphoid malignancies, and HIV-associated lymphadenopathies, etc.

In the methods of the present invention, phenylarsine oxide and phenylarsine oxide derivatives can be administered in any conventional way for treating an individual with a drug such as by injecting a solution containing phenyl arsine oxide or one or more phenylarsine derivatives into the bloodstream of an individual.

PAO (or its derivatives) can be removed completely with DMP(S) (or a related compound) once the goal of shedding is accomplished. Shedding can be easily monitored ex vivo, and these reversal drugs have been in use for years, and the reversal is supposed to be complete.

So, in principle, it is possible to treat a patient (HIV or inflammation or reperfusion problem) with PAO(*) and then remove it within minutes by chelating it with the various available versions of anit-Lewisite war gas reagent(s), making this a kind of a "pharma-co-surgical" procedure. Since this removal is specific for the arsenical, it will work on all PAO(*) derivatives described below.

Pharmacological formulation of calmodulin antagonists such as phenothiazine derivatives (e.g. chlorpromazine) and bis-chlorophenylethanes derivatives such as DDT display both the broad-spectrum anti-inflammatory and the specific anti-lymph-node homing properties with respect to leukocytes.

The present invention will now be described by way of example.

EXAMPLES

I. Detection of L-selectin Release

L-selectin release can be measured either as a loss of L-selectin from the cell surface using a fluorescence activated cell sorter (FACS), or it can be measured as an increase of the released, soluble L-selectin in the cells'supernate (using, for example, an ELISA).

A) Using FACS Analyzer

Using this method, cell-associated L-selectin is measured. Using fluorescently labeled anti-L-selectin antibody, the cell surface L-selectin is tagged. PDI inhibition causes L-selectin and its tag to be released from the cell surface. This results in a loss of cell-associated fluorescence.

There are two, essentially equivalent, methods for detecting the release of L-selectin from leucocyte cell surfaces.

In the first method, cells are first treated with the inhibitor and then samples are labeled individually for L-selectin that remains on the cell surface. In the second method, the cells are prelabeled with a fluorescent anti-L-selectin antibody and then treated with the putative PDI inhibitor. Prelabeling of the cells has only a minor accelerating effect on L-selectin shedding when the treatment times are in the range of 10 min. The temperature control sample, lacking any drug treatment, reflects this "spontaneous" shedding when compared with a prelabeled sample that was kept on ice. This method, however, permits the preparation of a large volume of uniformly prelabeled substrate cells for the assay, minimizes inter-sample variation, and is less labor intensive. Prelabeling of cells with a fluorescent anti-L-selectin antibody does not interfere with PDI inhibition or L-selectin shedding.

In either case, the cells are labeled with a fluorescent (e.g., FITC or PE) anti-L-selectin antibody on ice for 45 minutes at a concentration in the range of 1 mg/ml (see specific example below).

B) Using a Soluble L-selectin (sL-selectin) ELISA

This assay was validated using the Bender MedSystems (Boehringer Ingelheim Group, Vienna, Austria) sL-selectin ELISA kit. However, a much better source of sL-selectin ELISA kits is Endogen (Endogen, Inc. Woburn, MA). Measuring sL-selectin using ELISA rather than the FACScan analysis is a much more convenient method for screening large numbers and concentrations of various putative PDI inhibitors. Moreover, smaller numbers of leucocytes are required for this method. The one advantage of FACScan analysis over the ELISA is that toxicity to the cells is readily noted an the FSC/SSC FACScan output. Since acute toxicity could result in a PDI-independent loss of L-selectin release, selected sample analysis should be confirmed using the FACScan method.

Final validation of reagent PDI inhibitory activity is carried out inter alia, using purified PDI protein (Sigma) and one of the several standard PDI activity assays. One example of such an established PDI assay is based on the ability of PDI to renature, and thus restore activity to, RNAse A with scrambled disulfide bonds (Sigma) (*Methods in Enzymology*, 251:397–406, 1995). Only properly disulfide-bonded RNAse A is able to degrade RNA. The increase in absorbance at 260 nM is a reflection of RNAse activity. A control reaction mix containing only scrambled RNAse without PDI provides for a measure of the uncatalyzed RNAse renaturation. PDI inhibitors abolish RNAse renaturation and are displayed as a loss of 260 nM absorbance as compared to a control. This method, while highly specific and accurate, is very labor intensive and would prove very expensive for large-scale screening purposes.

II. Preparation of PDI Inhibitors

The putative PDI inhibitors are preferably dissolved in an aqueous solvent. PAO solutions (10 mM stock) are prepared in DMSO (Sigma Chemical Co.) and gently heated until PAO goes into solution. Other potential inhibitors of PDI are also dissolved in DMSO. DMSO concentration in the assays should not exceed 1% final volume; above this concentration, DMSO may affect L-selectin shedding. Dioxane should not be used, as it itself induces L-selectin release.

III. Discrimination Between PDI Inhibition and Cell Activation

Activation of neutrophils with a number of biologicals such as fMLP, PAF or LPS, results in the shedding of L-selectin in a manner that does not depend on a direct blockade of PDI activity. Since cell surface increase of Mac-1 integrin, a cell adhesion molecule, (CD18/CD11b) is characteristic of cell activation, reagents which act directly on PDI should not promote the upregulation of Mac-1 on neutrophils. The levels of Mac-1 can readily be measured by flow cytometry using fluorescently labeled anti-Mac-1 antibodies. Useful PDI inhibitors are preferably not cell-type specific. For example, fMLP and LPS only affect neutrophils but not lymphocytes, while preferred PDI inhibitors affect L-selectin shedding from both cell types.

IV. Interference with the Intracellular Calmodulin Pathway

Promotion of L-selectin shedding by interfering with calmodulin's binding to the intracellular tail of L-selectin is achieved by treating cells with calmodulin antagonists. L-selectin shedding induced by these reagents is inhibitable by the L-selectin sheddase inhibitors (e.g. TAPI) but not low micromolar concentrations of DMPS. Calmodulin is found in all cells, and calmodulin inhibition may have pleiotropic and potentially adverse effects. It is interesting that calmodulin antagonists such as chlorpromazine, potentially applicable for the induction of L-selectin shedding, and known to be safe for human use, are found to be effective at physiologically relevant concentrations of 10–50 uM.

Known Concepts

1) Direct Assay for Measuring Purified PDI Activity (Freeman R B, Hawkins H C, and McLaughlin S H, 1995 "Protein Disulfide Isomerase", *Methods in Enzymology* 251:397–406, 1995, the entire contents and disclosure of which is hereby incorporated by reference).

2) Flow Cytometric Analysis of Cell Associated L-selectin (Bennet T A, Lynam E B, Sklar L A, and Rogelj S. "Hydroxamate-base metalloprotease inhibitor blocks shedding of L-selectin adhesion molecule from leucocytes; functional consequences for neutrophil aggregation", *J. Immunol.* 156(9):3093–7, 1996, the entire contents and disclosure of which is hereby incorporated by reference).

3) ELISA for Quantitation of Soluble L-selectin (Spertini O, Schleiffenbaum B, White-Owen C, Ruiz P Jr., and Tedder T F, "ELISA for quantitation of L-selectin shed from leucocytes in vivo." *J. Immunol Methods* 156(1):115–23, 1992, the entire contents and disclosure of which is hereby incorporated by reference).

Example I

Neutrophil or Lymphocyte Isolation

Human venous blood was collected from healthy volunteers into sterile syringes containing heparin (10 U/ml blood, Elkins-Simms Inc., Cherry Hill, N.J.). The blood was separated on Mono-Poly resolving media (ICN Biochemicals, Aurora, Ohio) by centrifugation of 500 g for 22 minutes at 18° C. The granulocyte and mononuclear (for lymphocytes) layers were collected separately and washed in HHB buffer (110 mM NaCl, 10 mM KCl, 10 mM glucose, 1 mM $MgCl_2$ and 30 mM HEPES, pH 7.40), then pelleted at 400g for 10 minutes. The cells were resuspended in HHB buffer containing 0.1% human serum albumin (HSA; Armour Pharmaceutical Co., Kankakee, Ill.) and 1.5 mM $CaCl_2$, at $10^6$ cells/ml and kept on ice. The buffer was depleted of endotoxin by affinity chromatography over columns containing polymyxin B sepharose (Detoxi-gel, Pierce Scientific, Rockford, Ill.) and autoclaved for one hour. All plastic-ware was autoclaved for at least 45 minutes.

Snezna L-Selectin Shedding Assay

Cells suspended in HSA and $CaCl_2$ containing HHB at $10^6$ cells/ml were immunofluorescently labeled for 45 min on ice with Leu-8-FITC (IgG2a; Becton-Dickinson Monoclonal Antibodies, Lincoln Park, N.J.), a fluorescent mAb which recognizes L-selectin, at a final concentration of 0.625 μg/ml. 200 μl of this prelabeled cell suspension is used for each sample. The assay is preferably carried out in duplicate and contains:

| a) | Ice control. |
|---|---|
| b) | Temperature control. |
| c) | Solvent control: (b) + solvent of the drug to be tested. |
| d) | fMLP at 100 nM. |
| e) | a known PDI inhibitor, e.g. PAO or DTNB. |
| f) | Sample drugs at various concentrations (optional). |

Samples (b) onwards were placed into a waterbath at 37° C., for about 10 minutes. The reaction was terminated by placing and keeping the samples on ice. The relative expression of the receptors was quantitated using a FACScan Flow Cytometer (such as Becton-Dickinson).

Controls: To show that cells are viable and normally responsive, neutrophils were activated with fMLP (formyl-methionyl-leucyl-phenylalanine; Sigma chemical Co., St. Louis, Mo.) for 10 min at 37° C. at a final concentration of 100 nM. This releases at least 90% of all cell surface L-selectin as measured by the loss of fluorescently labeled L-selectin from neutrophils using FACScan. Lymphocytes do not respond to fMLP. Lymphocytes do shed their L-selectin in response to phorbol ester PMA (100 nM), but do so only slowly (~30 min). To show that leucocytes respond normally to PDI inhibitors, the response of both neutrophils and lymphocytes to μM concentrations of phenylarsine oxide (PAO, Sigma) was measured: Neutrophils shed most of their L-selectin in response to 1 μM PAO within 10 min; lymphocytes required 5μM PAO to shed their L-selectin within 20 min. Alternatively, a known blocker of PDI, 5',5'-dithio-bis(2-nitrobenzoic acid) (DTNB, Sigma), can be used at 1 mM concentration as a positive control.

To check for cell activation, the neutrophils are assayed for the characteristic increase in the cell surface Mac-1 expression. This is done by carrying out the above L-selectin shedding assay, but using unlabeled cells. At the end of the 37° C. incubation period, neutrophils are placed on ice and Leu-15-PE (IgG2a; Becton-Dickinson Monoclonal Antibodies), a fluorescent mAb which recognizes the α-subunit (CD11b) of Mac-1, is added at the final 1.25 μg/ml concentration. Samples are incubated with the antibody on ice for 45 minutes, and expression of the receptors thereafter quantitated with the FACScan. An fMLP-treated sample served as a positive control; samples treated with fMLP increased their cell surface expression 3–10 fold compared to the ice control.

The effect of the putative PDI inhibitors on other cell surface molecules was further assessed using either analogous direct immunofluorescence or indirect immunofluorescence. For example, after the treatment of unlabeled cells with the appropriate reagents, the cells were incubated for 40 minutes at 4° C. with appropriate antibodies. The antibodies against CD14, CD16 (both at 10 μg/ml; Dako Corporation, Carpinteria, Calif.), CD43 (μg/ml; IgG2a; Camfolio (Becton-Dickinson), San Jose, Calif.), CD54 (μg/ml; Biosource International, Camarillo, Calif.), PSGL-1 (PL1;IgG1; 10 μg/ml; Dr. Rodger McEver, University of Oklahoma). After incubation the cells were washed by centrifugation for 10 minutes at 400g at 4° C. The second antibody, goat-anti-mouse IgG-FITC (GAM-FITC) polyclonal Ab (Becton-Dickinson Antibodies, Lincoln Park, N.J.) at a concentration of 6.25 μg/ml was added and cells were incubated an additional 20 minutes at 4° C. After a final wash, the specific labeling for each antibody was analyzed by flow cytometry.

Time Course Experiments

For these experiments, isolated neutrophils or lymphocytes were warmed to 37° C. and a zero point sample was withdrawn and placed on ice. The putative PDI inhibitor was then added. Cell samples were withdrawn at one minute intervals and placed on ice. The cells were then labeled for 40 minutes with Leu8-FITC on ice and L-selectin expression measured by the FACScan.

Example II

General Protocol for Directly Assessing the Ability of PDI Inhibitors to Block HIV Entry into Cells The protocol used by NIH, Department of Health and Human Service "Anti-HIV Drug Testing system" infra is designed to detect agents acting at any stage of the virus reproductive cycle. As is pointed out in this description of the test, certain compounds may not show activity in this test. Inhibitors of PDI, such as PAO and its derivatives, act at the stage of the viral entry which occurs within the first few (2–3) hours of the contact between the viral stock and the target cells. To assay for the specific impact of a drug on viral entry, both the drug and the free virion should be removed from the cells after the infection period. The decrease in the number of the infected cells after the 6 days incubation period will be a reflection on the drug's inhibition of viral entry. This variation on the NIH protocol will additionally eliminate the potential toxic effects associated with the long-term exposure of the drug. The impact of inhibitors on HIV entry may otherwise be obscured by such long-term toxicity. In the case of PAO/PAO* a long-term toxicity was anticipated and in spite of the superimposition of long-term toxicity onto the outcome, PAO* did show anti-HIV activity in this assay. It is expected that about ~10 uM PAO* will show a complete blockade of HIV entry when the above steps are followed in the protocol. PAO and other analogues are likely to have a similar effect.

Knowledge that a reagent (a PDI inhibitor) is effective at inhibiting the viral entry is of great value; and changes in drug design according to known principles can subsequently minimize potential toxicities. Since the target of inhibition is PDI, a cell surface protein, this may in many cases only require making the drug less membrane permeable. This is true in the case of PAO, which, when made less membrane permeable (PAO*), nonetheless shows anti-HIV activity. Moreover, there are clinical situations which may require only a short exposure to the drug which blocks HIV entry and where long-term treatment may not be necessary. One example would be treatment of an individual only recently infected with HIV, as by a stick with an infected needle.

NIH Anti-HIV Drug Testing System

The procedure‡ used in the National Cancer Institute's test for agents active against human immunodeficiency virus (HIV) is designed to detect agents acting at any stage of the virus reproductive cycle. The assay basically involves the killing of T4 lymphocytes by HIV. Small amounts of HIV are added to cells, and two cycles of virus reproduction are necessary to obtain the required cell killing. Agents that interact with virions, cells, or virus gene-products to interfere with viral activities will protect cells from cytolysis. The system is automated in several features to accommodate large numbers of candidate agents and is generally designed to detect anti-HIV activity. However, compounds that degenerate or are rapidly metabolized in the culture conditions may not show activity in this screen. All tests are compared with at least one positive (e.g., AZT-treated) control done at the same time under identical conditions.

The Procedure

1. Candidate agent is dissolved in dimethyl sulfoxide (unless otherwise instructed) then diluted 1:100 in cell culture medium before preparing serial half-log$_{10}$ dilutions. T4 lymphocytes (CEM cell line) are added and after a brief interval HIV-1 is added, resulting in a 1:200 final dilution of the compound. Uninfected cells with the compound serve as a toxicity control, and infected and uninfected cells without the compound serve as basic controls.

2. Cultures are incubated at 37° C. in a 5% carbon dioxide atmosphere for 6 days.

3. The tetrazolium salt, XTT, is added to all wells, and cultures are incubated to allow formazan color development by viable cells.

4. Individual wells are analyzed spectrophotometrically to quantitate formazan production, and in addition are viewed microscopically for detection of viable cells and confirmation of protective activity.

5. Drug-treated virus-infected cells are compared with drug-treated noninfected cells and with other appropriate controls (untreated infected and untreated noninfected cells, drug-containing wells without cells, etc.) on the same plate.

6. Data are reviewed in comparison with other tests done at the same time and a determination about activity is made.

‡Weislow, O. W., Kiser, R., Fine, D., Bader, J., Shoemaker, R. H., Boyd, M. R.: New soluble-formazan assay for HIV-1 cytopathic effects: application to high-flux screening of synthetic and natural products for AIDS-antiviral activity. J. Natl. Cancer Inst. 81;577–586, 1989.

Example III

1. Preparation of PAO*

Membrane impermeable derivatives of PAO were designed, prepared, and tested. These derivatives, referred to herein as PAO*s, have a charged ligand attached to the aromatic amine of 4-aminophenylarsenoxide (4-APAO). The charge on this terminal ligand is believed to prevent the molecule from passing through the cell membrane.

A number of potential synthetic PAO* targets exist. In the planning of these preparations, the difficulties of working with organometallic reagents must be noted. First, conditions must be selected so that the arsenic is not inadvertently oxidized from As(III) to As(V). Second, because of the metal content as well as the charged portion of the PAO* molecule, many standard organic chemistry purification and characterization techniques are inoperable.

The first PAO* derivative was prepared through the reaction of 4-APAO with 2-bromoethanesulfonic acid sodium salt in 1:1 DMSO:water. This was carried out in the presence of aqueous Na$_2$CO$_3$ at 90° C. for 8–12 hours.

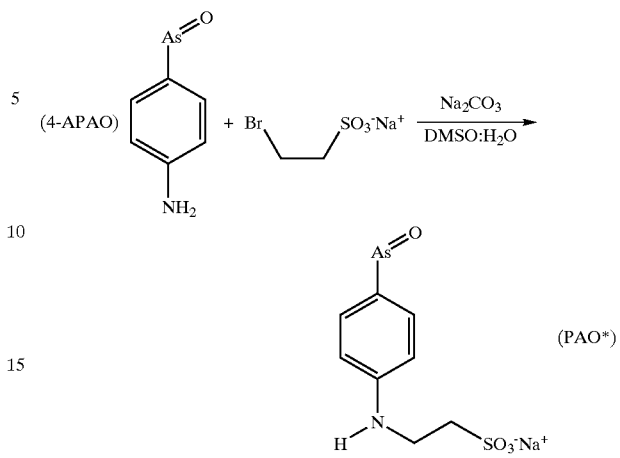

Column and thin layer chromatographies for purification and purity assessment do not work with this system. Gas chromatography-mass-spectrometry as well as more direct mass spectrometry ionization methods have also proven ineffective due to the low volatility of the tested compound. Reversed phase HPLC using ocratic water and UV detection provided a reasonable assay for this first PAO* derivative. Along with proton NMR analysis, data confirmed both the structure and purity of PAO*.

2. Additional Versions of PAO*

Figure 2:
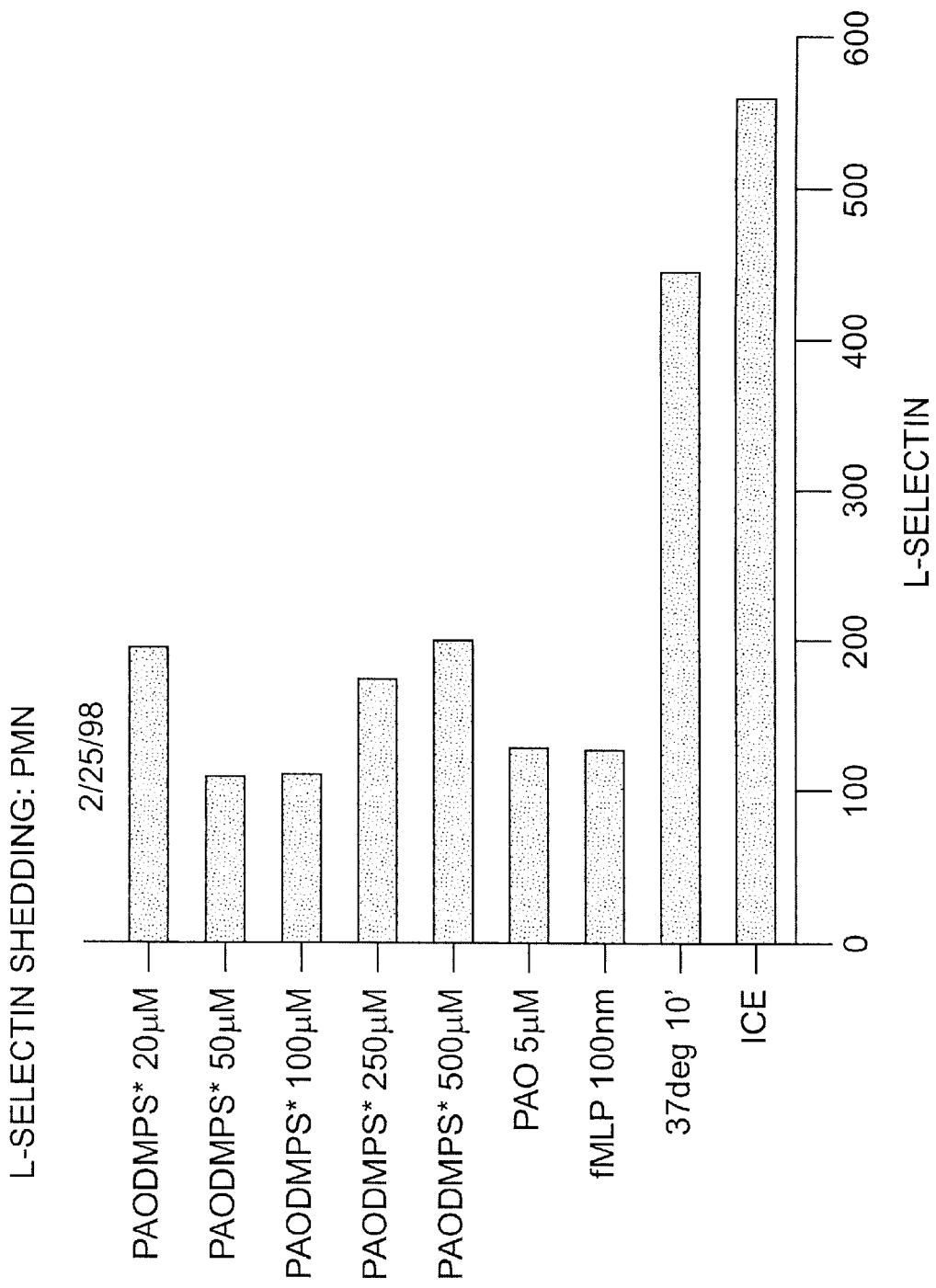
FIG. 2. Induction of L-selectin shedding with PAOD-MPS*.
Figure 3:
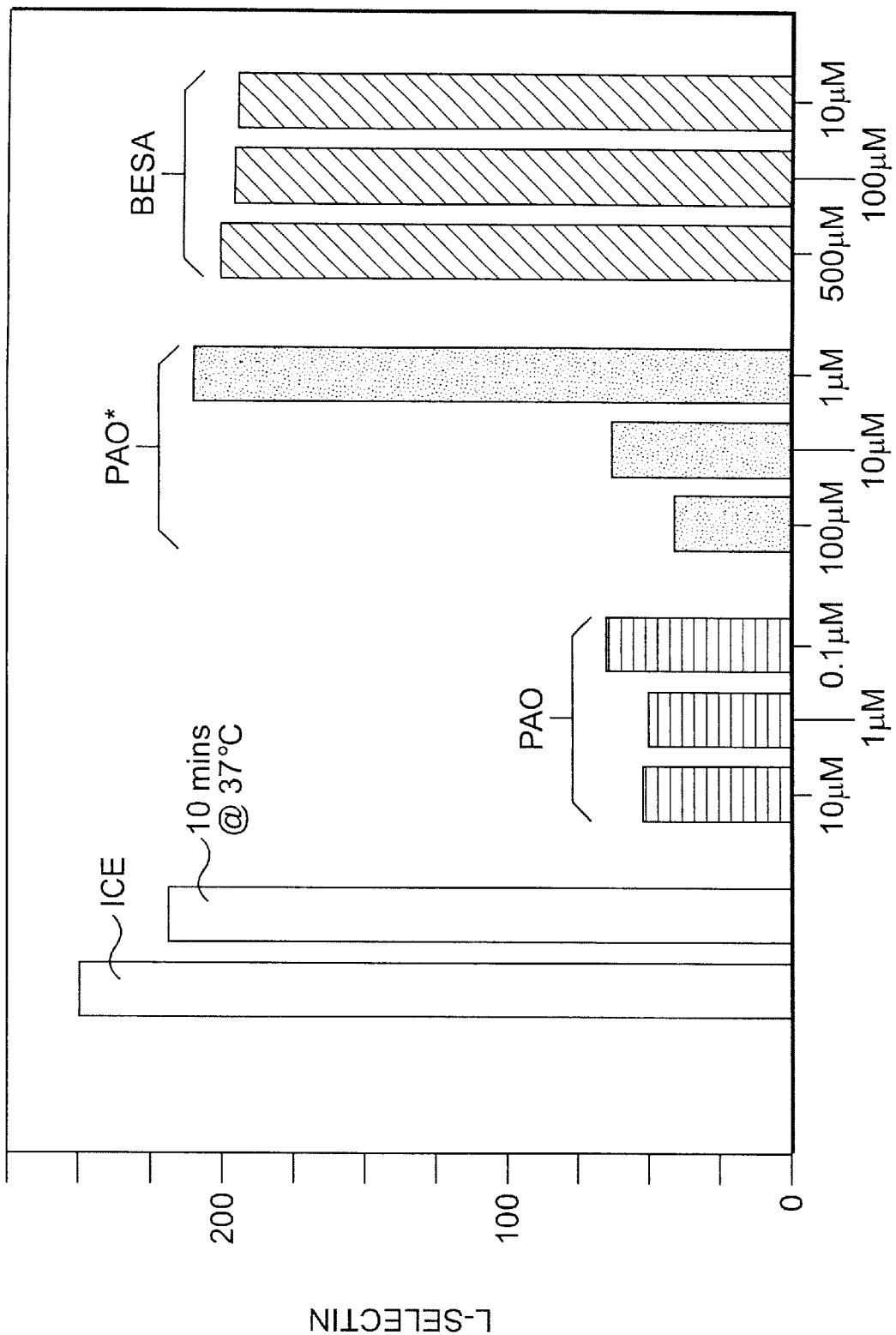
FIG. 3. Effect of PAO, PAO* and BESA on L-selectin shedding from human neutrophils.

An additional membrane-impermeable derivative of PAO*, PAODMPS* was prepared according to the following reaction scheme. The compound was shown to induce L-selectin shedding (FIG. 2).

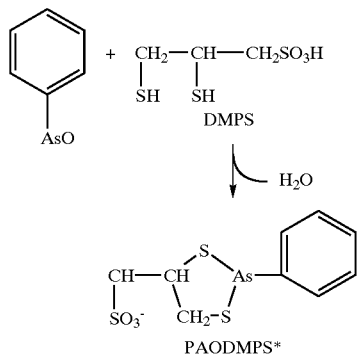

Following the successful purification of this initial PAO* derivative, other PAO* derivatives are prepared and tested.

The following chemical modifications are particularly interesting:

Compound A

The addition of more than one charged entity to the prototypical PAO molecule may impart a further decrease in membrane permeability. Compound A has two anionic SO$^3$- groups:

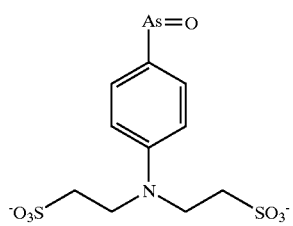
(A)

Compound B

The addition of alkyl chains of various lengths between the amino nitrogen and the charged group may impart varying degrees of partial membrane impermeability. The longer chains may allow the aromatic portion of the compound to permeate the membrane while the charged portion of the molecule remains outside the membrane. Various chain lengths allow for various depths of penetration through the membrane.

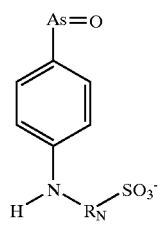
(B)

wherein $R_N$ is $C_{1-8}$ alkyl most preferably $C_1$, $C_3$, $C_4$ or $C_6$ alkyl.

Compound C

Additional control over molecular geometry may be obtained by the incorporation of a more rigid aromatic ligand bearing the charged entity. This allows for a more specific control over sterics and electronics than is allowed through the use of simple alkyl chains.

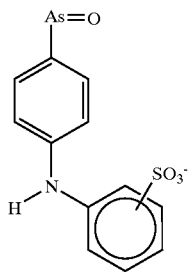
(C)

Compound D

Negatively charged ligand: A quaternary ammonium salt imparts a positive charge to the ligand. The implications of positive versus negative charges on the PAO* ligand have not yet been examined in this system.

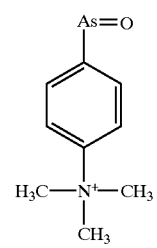
(D)

Compound E

The phenyl ring in 4-amino PAO can be replaced with hetero-aromatic substituents, such as an isoxazolyl ring. The isoxazole is well known in medicinal chemistry to be amenable to a variety of substitution patterns. Furthermore, an isoxazole can be heterolytically cleaved to the acylaziridine using photochemistry and therefore may be useful as a photoaffinity probe.

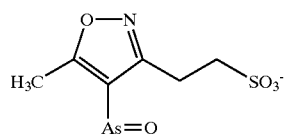
(E)

Derivatives A', B', C', D', and E' of Compounds A, B, C, D, E, respectively can be formed having the following general formulas

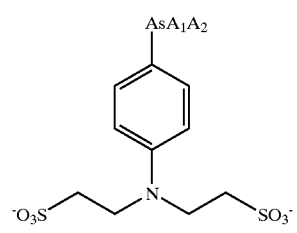
(A')

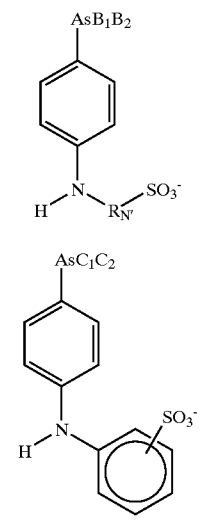
(B')

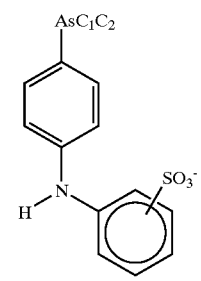
(C')

-continued

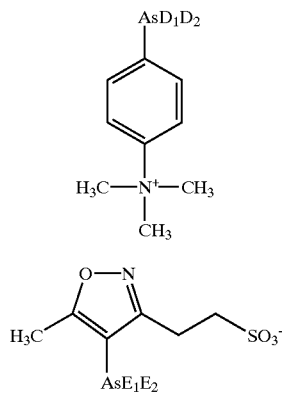
(D')

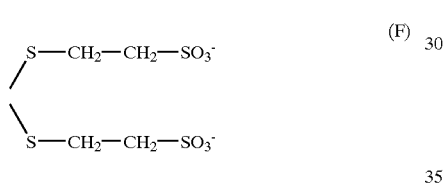
(E')

wherein $A_1$, $A_2$, $B_1$, $B_2$, $C_1$, $C_2$, $D_1$, $D_2$, $E_1$, and $E_2$ are each a ligand conjugated through as and $R_N$ is $C_{1-8}$ alkyl, preferably $C_1$, $C_3$, $C_4$, or $C_6$ alkyl.

Reacting compound A, B, C, D, and E with Beta-mercaptopropane sulfonic acid, results in compounds A'F. , B'F. , C'F. , D'F. , and E'F. , shown below, where ligand combinations $A_1$ and $A_2$, $B_1$ and $B_2$, $C_1$ and $C_2$, $D_1$ and $D_2$, and $E_1$ and $E_2$, of compounds A', B', C', D' and E', respectively, are ligand F. below:

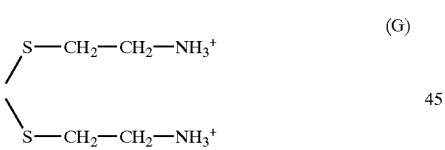
(F)

Reacting compounds A, B, C, D, and E with Cysteamine HCl, results in compounds A'G, B'G, C'G, D'G, and E'G, shown below, where ligand combinations $A_1$ and $A_2$, $B_1$ and $B_2$, $C_1$ and $C_2$, $D_1$ and $D_2$, and $E_1$ and $E_2$, of compounds A', B', C', D' and E', respectively, are ligand G below:

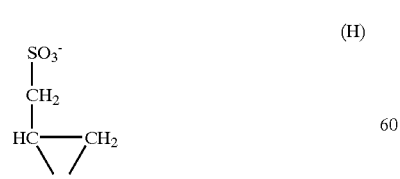
(G)

Reacting compound A, B, C, D, and E with Dimercaptopropane sulfonic acid, results in compounds A'H, B'H, C'H, D'H, and E'H, shown below, where ligand combinations $A_1$ and $A_2$, $B_1$ and $B_2$, $C_1$ and $C_2$, $D_1$ and $D_2$, and $E_1$ and $E_2$, of compounds A', B', C', D' and E', respectively, are ligand H below:

(H)

Examples of compounds A', B', C', D', and E' where ligand combinations $A_1$, and $A_2$, $B_1$ and $B_2$, $C_1$ and $C_2$, $D_1$ and $D_2$, and $E_1$ and $E_2$, are ligands F, G and H, respectively, are illustrated below:

Compound A'F below is compound A' where ligand combination $A_1$ and $A_2$ is F:

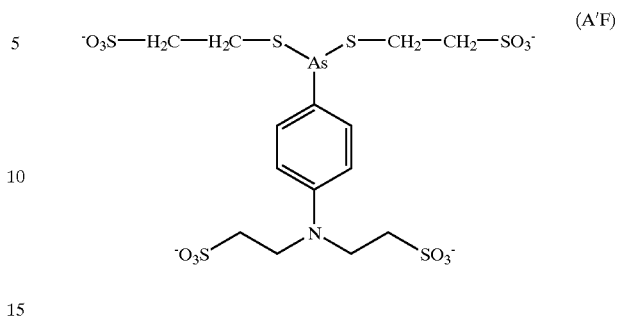
(A'F)

Compound A'G below is compound A' where ligand combination $A_1$ and $A_2$ is G:

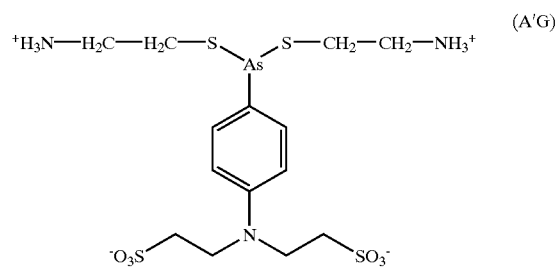
(A'G)

Compound A'H below is compound A' where ligand combination $A_1$ and $A_2$ is H:

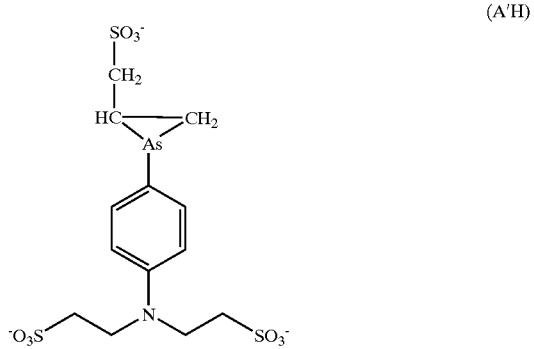
(A'H)

Compound B'F below is compound B' where ligand combination $B_1$ and $B_2$, is F:

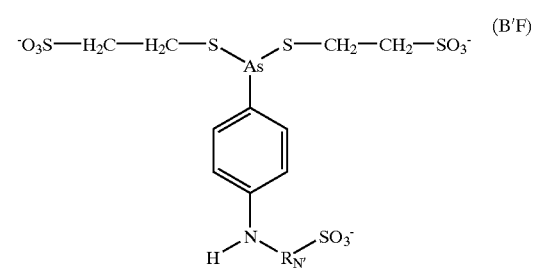
(B'F)

Compound B'G below is compound B' where ligand combination $B_1$ and $B_2$ is G:

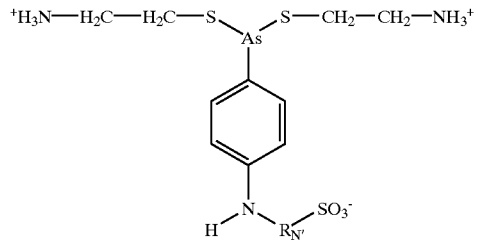
(B'G)

Compound B'H below is compound B' where ligand combination $B_1$ and $B_2$ is H:

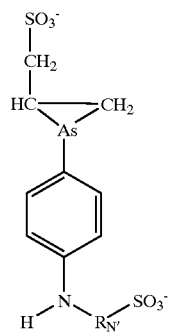
(B'H)

Compound C'F below is Compound C' where ligand combination $C_1$ and $C_2$ is F:

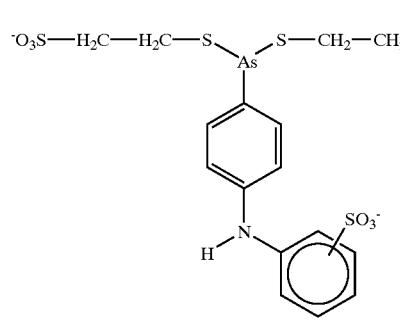
(C'F)

Compound C'G below is Compound C' where ligand combination $C_1$ and $C_2$ is G:

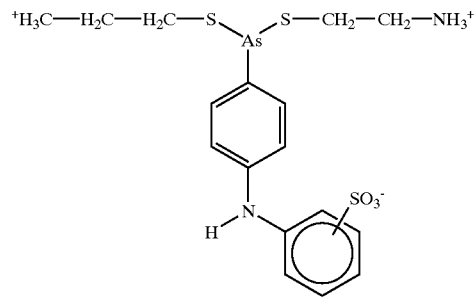
(C'G)

Compound C'H below is Compound C' where ligand combination $C_1$ and $C_2$ is H:

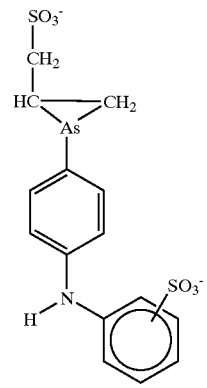
(C'H)

Compound D'F below is Compound D' where ligand combination $D_1$ and $D_2$ is F:

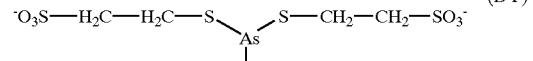
(D'F)

Compound D'G below is compound D' where ligand combination $D_1$ and $D_2$ is G:

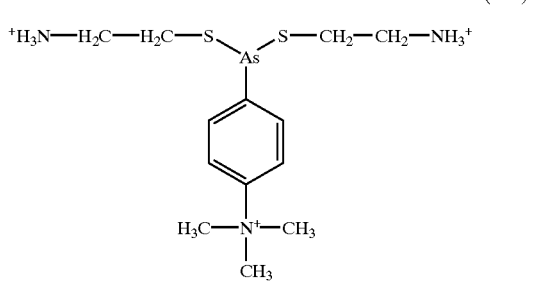
(D'G)

Compound D'H below is Compound D' where ligand combination $D_1$ and $D_2$ is H:

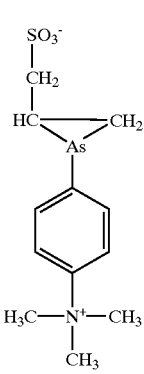
(D'H)

Compound E'F below is compound E' where ligand combination $E_1$ and $E_2$ is F:

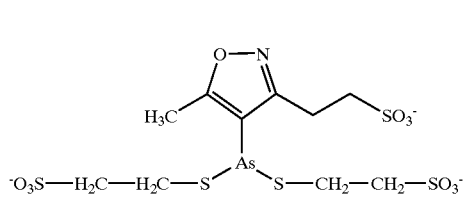
(E'F)

Compound E'G below is Compound E' where ligand combination $E_1$ and $E_2$ is G:

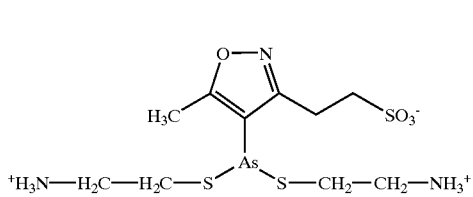
(E'G)

Compound E'H below is Compound E' where ligand combination $E_1$ and $E_2$ is

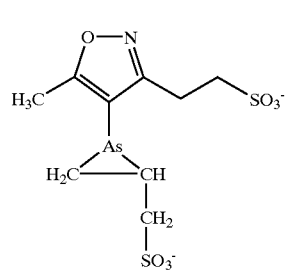
(E'H)

A novel class of membrane-impermeable arsenoxide derivatives is generated on this basic principle. Conjugation of a membrane-impermeable compound to the arsenical via (di)thiols makes the compound membrane-impermeable until the compound reacts with the vicinal dithiol of PDI and the original adduct is reduced and released extracellularly. By conjugating ligands F-H to form membrane-impermeable PAO* derivatives, the derivative is fully restricted to the outside of the cells and non-toxic. The number of anti-trypanosomal drugs have been generated on this chemical principle (*Eur. J Biochem*, 221:285–95, 1994), but with one important difference: these anti-trypanosomal drugs need to enter the cells, so both sides of the active site arsenical are made extra membrane-permeable.

Example IV

Method for Whole Blood Measurement of Inhibitor-Activity

Figure 4A:
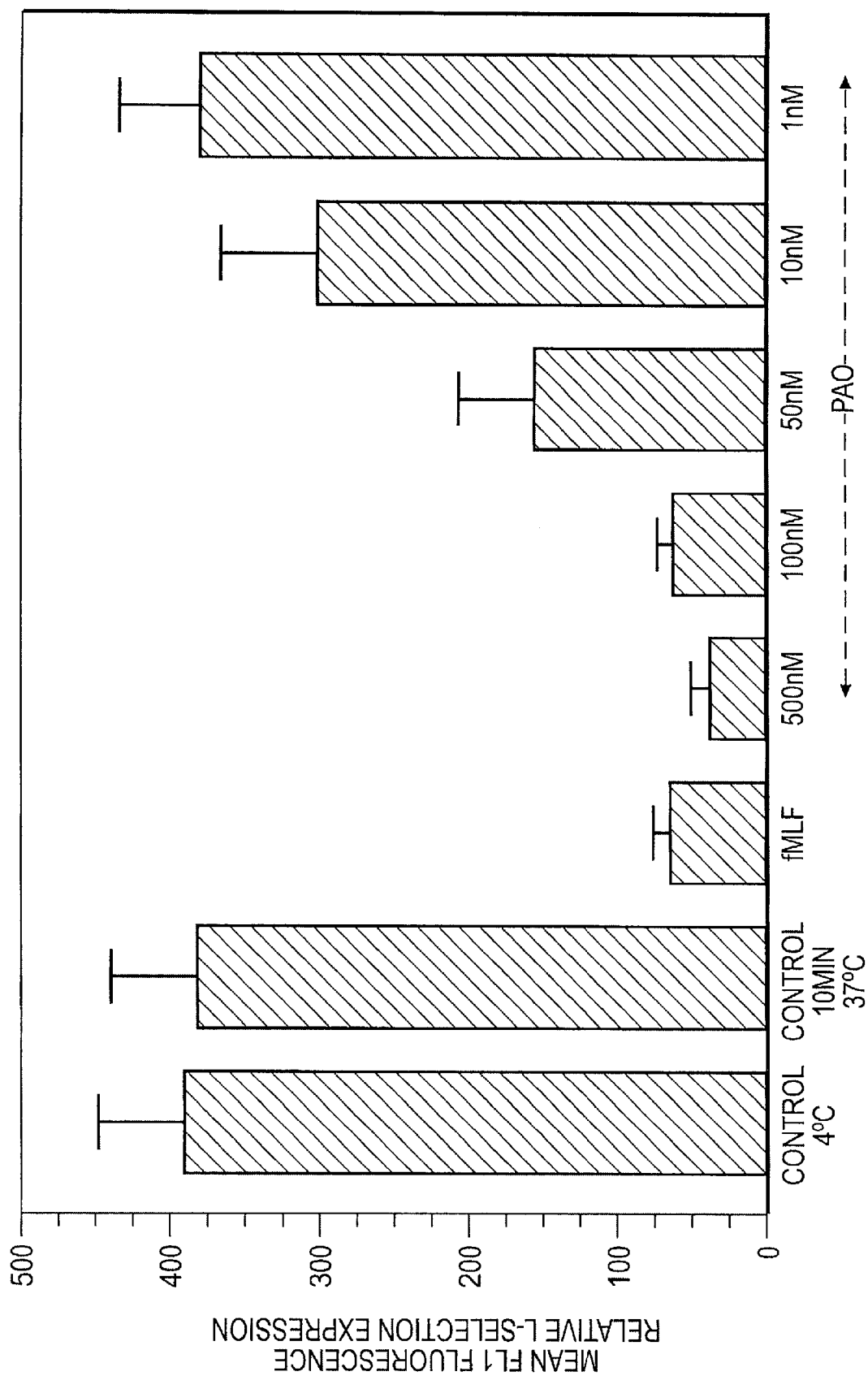
FIG. 4. Effect of PAO on neutrophil adhesion molecules (a) PAO induces L-selectin shedding from neutrophils in a dose dependent manner. Control-4° C. represents a neutrophil population that has remained at 4° C. since isolation. L-selectin levels were normalized, with the expression on the Control-4° C. population representing 100%. Control-10 min. @ 37° C. is an untreated population that underwent a mock 10 minute incubation along with the PAO and/or fMLP treated cells. (b) A phenotypic analysis of PAO treated neutrophils. 100 nM PAO does not appreciably upregulate Mac-1 or induce the shedding of other cell surface molecules known to undergo proteolytic cleavage. The mean channel number of fluorescence is reported with the S.E.M. Experiments were performed twice with duplicate or triplicate samples done in each. (c) *Activity in whole blood.* Peripheral venous blood was diluted 1:10 with HHB buffer and treated with 1 μM PAO for 20 minutes at 37° C. L-selectin expression was measured by the subsequent FAC-Scan analysis of the LDS-751 and Leu8-FITC labeled cells.
Figure 4C:
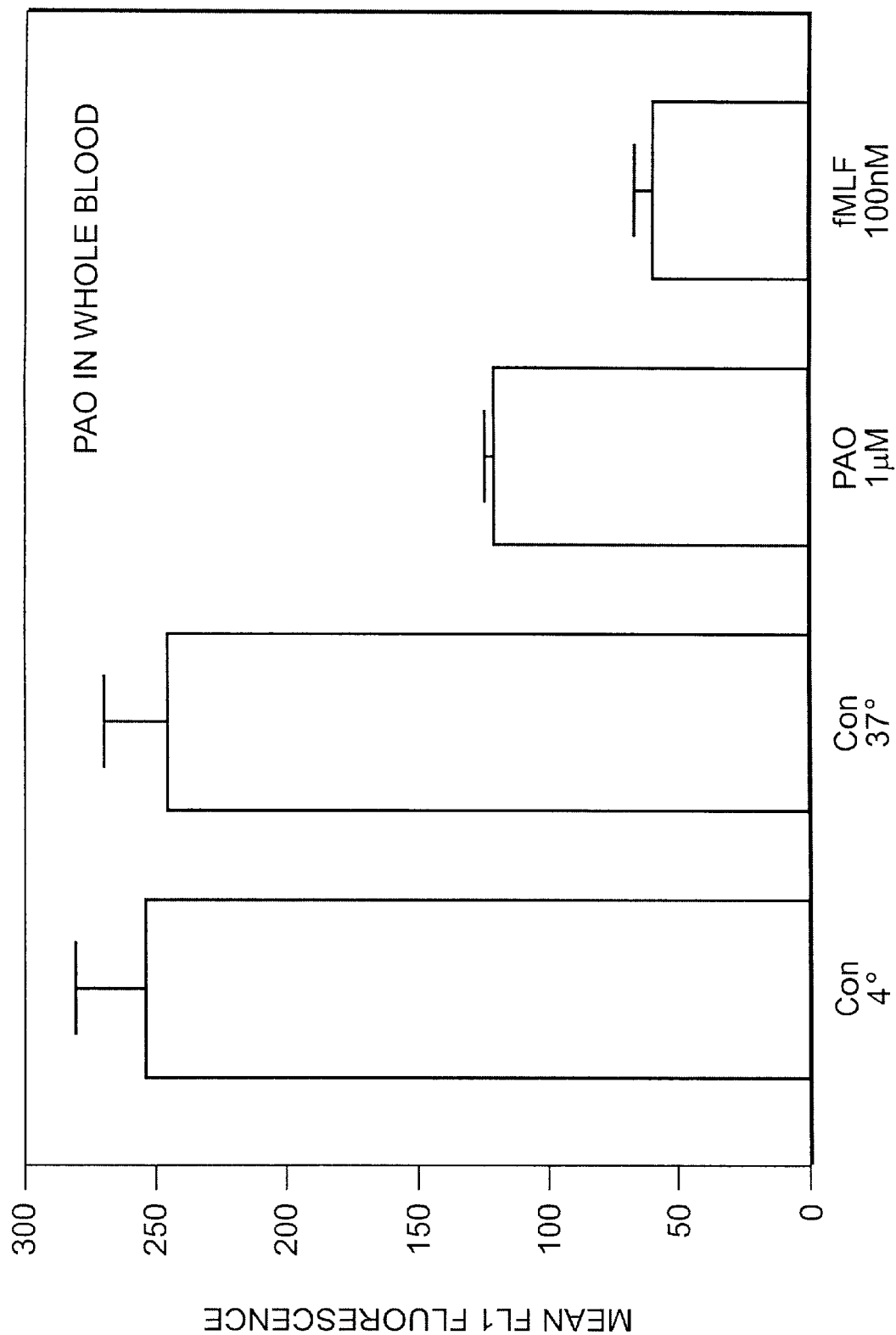

Inhibitor in whole blood can be measured as follows:

Peripheral venous blood was diluted 1:10 with HHB buffer and treated with 1 $\mu$M PAO for 20 min. at 37° C. L-selectin expression was measured by FACScan analysis (supra) of LDS-751 and Leu8-FITC labelled cells (FIG. 4). For HIV treatment, activity is preferably measured by L-selectin expression on lymphocytes, rather than neutrophils.

Induction of L-selectin shedding in whole blood is useful as an assay to determine the inhibitor concentration required to block, e.g., leucocyte or lymphocyte PDI. This whole-blood ex-vivo assay is preferable to assays of purified leucocytes or lymphocytes for clinical use of the inhibitors.

What is claimed is:

1. A method for treating an inflammatory disease comprising:

administering an anti-inflammatory agent to an individual in an amount sufficient to reduce an inflammation in the individual, wherein the anti-inflammatory agent comprises a compound having the formula:

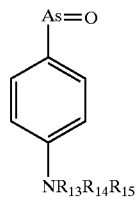

wherein each of $R_{13}$, $R_{14}$, and $R_{15}$ is nothing, H, alkyl, alkyl sulfonate, or aromatic sulfonate.

2. The method of claim 1, wherein the anti-inflammatory agent comprises a compound having the formula:

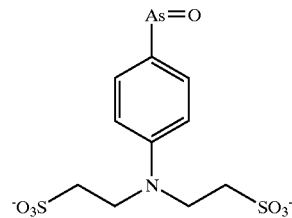

3. The method of claim 1, wherein the anti-inflammatory agent comprises a compound having the formula:

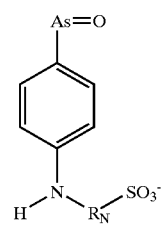

wherein $R_N$ is $C_{1-8}$ alkyl.

4. The method of claim 3, wherein $R_N$ is $C_1$, $C_3$, $C_4$ or $C_6$ alkyl.

5. The method of claim 1, wherein the anti-inflammatory agent comprises a compound having the formula:

27
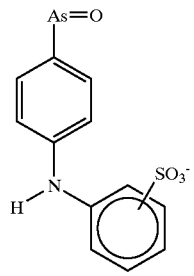
6. The method of claim 1, wherein the anti-inflammatory agent comprises a compound having the formula:
28
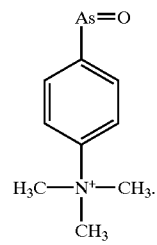
* * * * *